United States Patent [19]

Giordano et al.

[11] Patent Number: 5,053,533

[45] Date of Patent: Oct. 1, 1991

[54] PROCESS FOR PREPARING NAPROXEN

[75] Inventors: Claudio Giordano, Monza; Marco Villa, Milan, both of Italy

[73] Assignee: Zambon Group SPA, Italy

[21] Appl. No.: 223,377

[22] Filed: Jul. 25, 1988

[30] Foreign Application Priority Data

Jul. 28, 1987 [IT] Italy .............................. 21485 A/87

[51] Int. Cl.$^5$ ............................................. C07C 62/06
[52] U.S. Cl. .................................................. 562/466
[58] Field of Search ................ 562/418, 466; 568/323, 568/322

[56] References Cited

U.S. PATENT DOCUMENTS 3,821,253  6/1974  Fried .................................... 562/466
4,107,439  8/1978  Walker ................................. 562/466
4,328,356  5/1982  Giordana ............................. 562/466
4,697,036  9/1987  Giordano ............................. 562/418
4,868,338  9/1989  Magni et al. ........................ 568/319

FOREIGN PATENT DOCUMENTS 0163338  10/1985  European Pat. Off. .
9051234  3/1984   Japan .

Primary Examiner—Paul J. Killos
Attorney, Agent, or Firm—Parkhurst, Wendel & Rossi

[57] ABSTRACT

A process for preparing alpha-arylalkanoic acids is described, and more specifically a process which is particularly convenient from the industrial aspect for the synthesis of S(+)2-(6-methoxy-2-naphthyl)-1-propionic acid.

1 Claim, No Drawings

PROCESS FOR PREPARING NAPROXEN

This invention relates to an industrial form of a process for preparing alpha-arylalkanoic acids and more specifically a process particularly convenient for the synthesis of S(+)-2-(6-methoxy-2-naphthyl)-propionic acid.

Said compound, known as naproxen, is a medicament possessing anti-inflammatory and analgesic activity.

Various processes are known for preparing naproxen, most of which include the preparation of 2-(R,S)-2-(6-methoxy-2-naphthyl)-propionic acid or its precursors and the resolution of the raceme with optically active bases to isolate the S(+) enantiomer.

European patent application No. 158,913 in the name of Zambon S.p.A. describes an enantioselective process which enables the S(+) enantiomer to be obtained directly without any resolution.

One embodiment of this process can be schematized as follows:

1) Friedel-Crafts reaction between a naphthalene derivative of formula:

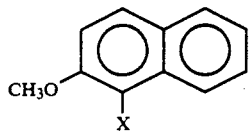

in which X=H, Cl or Br and propionyl chloride ($CH_3$-$CH_2$-CO-Cl) to obtain a compound of formula:

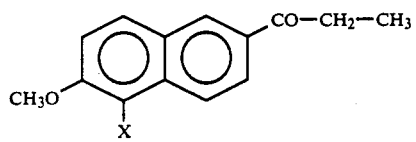

(in which X has the aforesaid meanings).

2) Ketalisation of the compound of formula II with natural tartaric acid or its derivatives to obtain a compound of formula:

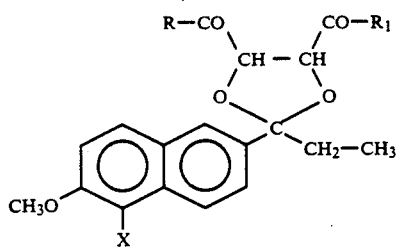

in which R and $R_1$, which can be identical or different, represent a hydroxyl, an alkoxy, a possibly substituted amino group, or an $O^-M^+$ group where $M^+$ represents the cation of an alkaline or alkaline-earth metal or ammonium; X has the aforesaid meanings; and the carbon atoms indicated by an asterisk both have R configuration.

3) Diastereoselective halogenation of the compound III, such as bromination, to obtain a compound of formula

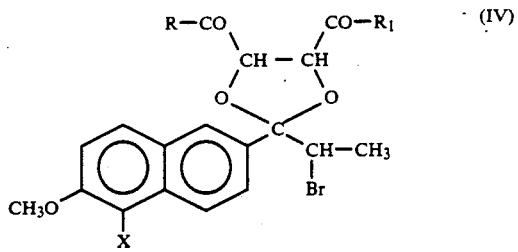

in which R, $R_1$ and X have the aforesaid meanings; the carbon atoms indicated by an asterisk both have R configuration; and the aliphatic carbon atom carrying the bromine atom has mainly S configuration.

4) Rearrangement of the compound IV in water at acid pH to obtain naproxen (X=H) or a precursor of formula

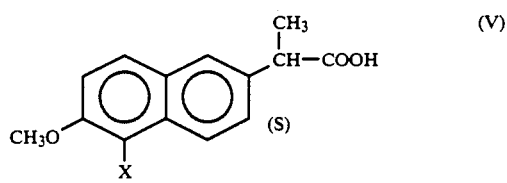

(in which X has the aforesaid meanings).

5) Possible hydrogenolysis of the halogen atom in position 5 of the naphthalenic nucleus (X=Cl, Br).

The aforesaid process, which as stated represents one embodiment of the process described in European patent application No. 158,913, is easily industrialised to satisfactorily provide naproxen with high yields and high optical purity.

However, in industrialising a process there is a continuous tendency to seek practical conditions which make the implementation of a process ever simpler or more convenient. These conditions may be for example the operating conditions themselves or particular expedients which enable yields to be increased, or which obviate the need to isolate and purify intermediates, or which enable a number of steps of the process to be carried out in a single reaction environment (reactor). If one or more of the aforesaid industrial improvements is attained, the result is an immediate economical advantage in terms of the cost of the final product.

We have now found that if step 1) of the aforesaid process (Friedel-Crafts reaction) is carried out using 1-chloro-2-methoxy-naphthalene (I, X=Cl) is used as the starting substrate, compound II (X=Cl) is obtained with such a high yield and purity that it is possible to proceed to the next step without isolating the compound obtained, and to conduct the next reaction (ketalisation) in the same reaction environment.

It is clear to an expert of the art that not having to isolate and purify an intermediate in an industrial synthesis is an important advantage in terms of the industrial product cost.

As the compound II in which X=Cl also represents an intermediate which is useful in the execution of industrial processes for preparing naproxen other than the aforesaid, such as those including the preparation of a raceme (see for example European patent No. 35,305) and its resolution, our discovery can be useful in a general naproxen preparation process, whether it comprises the aforesaid steps or the preparation of a raceme to be resolved.

The present invention therefore provides a naproxen preparation process which comprises preparing the compound 1-(5-chloro-6-methoxy-2-naphthyl)-1-propanone of formula:

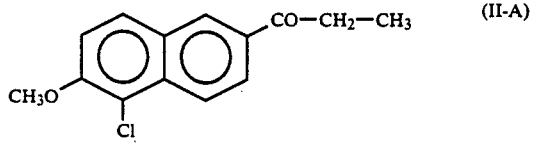

(II-A)

by a Friedel-Crafts reaction between propionyl chloride and 1-chloro-2-methoxy-naphthalene in methylene chloride in the presence of aluminium trichloride.

The reaction is preferably conducted at a temperature of between 0° C. and ambient.

Compared with the preparation of analogues of the compound II-A, ie 1-(6-methoxy-2-naphthyl)-1-propanone (II, X=H) and 1-(5-bromo-6-methoxy-2-naphthyl)-1-propanone (II, X=Br) by a Friedel-Crafts reaction between propionyl chloride and, respectively, 2-methoxy-naphthalene and 1-bromo-2-methoxy-naphthalene, the following advantages are obtained:

operating conditions which are immediately attainable industrially, with operating advantages such as the temperature range of between 0° C. and ambient in contrast to the other substrates for which it is necessary to operate at −20° C.;

a higher yield (specifically about 5-10% more than for compound II, X=H);

shorter reaction time;

reaction product with lesser impurity than compound II, X=Br, because the bromine atom in position 5 is more mobile under Friedel-Crafts conditions and often leads to the formation of undesirable by-products;

reaction products usable for the next reaction (ketalisation) without isolation and without the need for further purification;

similar ease of removal of the chlorine atom in position 5 under catalytic reduction conditions in the subsequent stages of the process as the removal of the bromine atom.

When applied to the aforesaid process, the process step according to the present invention is followed by a ketalisation step to obtain a compound of formula III in which X=Cl, a bromination step to obtain a compound of formula IV in which X=Cl, a rearrangement step to obtain (2S)-2-(5-chloro-6-methoxy-2-napthyl)-propionic acid and a hydrogenolysis step to eliminate the chlorine atom in position 5 and hence obtain naproxen.

In addition to the preparation advantages compared with analogous compounds and the advantages directly related to the implementation of an industrial process for naproxen synthesis, it must be emphasized that the compound 1-chloro-2-methoxy-naphthalene can be prepared very simply at industrial level starting from a low-cost industrial product, namely beta-naphthol.

This preparation which forms the second subject of the invention is carried out in a single reaction environment (reactor) by reacting beta-naphthol with a methylating agent to obtain 2-methoxy-naphthalene and then chlorinating this in the same reaction environment to obtain with practically quantitative yield the 1-chloro-2-methoxy-naphthalene, which can be used as such in the subsequent Friedel-Crafts reaction. The entire process is carried out in methylene chloride. The preferred methylating agent is methyl sulphate and the preferred chlorinating agent is an alkaline hypochlorite, chlorine or sulphuryl chloride.

EXAMPLE 1

A solution of 1-chloro-2-methoxy-naphthalene (4.8 g; 25 mmoles) in methylene chloride (15 ml) are added dropwise under agitation over 30 minutes to a mixture of aluminium trichloride (4.3 g; 32 mmoles), methylene chloride (20 ml) and propionyl chloride (2.9 g; 31 mmoles) cooled to 0° C. When the addition is complete the temperature is allowed to rise spontaneously to 20° C. The reaction is followed by TLC to confirm the disappearance of the starting substance (eluent hexane:ethyl ether=8:2).

The reaction terminates after 1 hour. The reaction mixture is poured into a mixture of conc. HCl (15 ml), ice (30 g) and water (20 ml). The phases are separated. The aqueous phase is separated with methylene chloride (25 ml). The pooled organic phases are dried over sodium sulphate. The solvent is eliminated under reduced pressure to obtain 6 g of residue (GLC purity 96%, 23.3 mmoles) of 1-(5-chloro-6-methoxy-2-naphthyl)-propan-1-one.

Characteristics: $^1$H-NMR (300 MHz-CDCl$_3$) delta (ppm): 1.28 (3H, t, J=7.5 Hz); 3.1 (2H, q, J=7.5 Hz); 4.06 (3H, s); 7.33-8.4 (5H, m, aromatic);

M.P.=135°-137° C. for crude product;

M.P.=137°-138° C. when crystallized from ethyl acetate.

We claim:

1. An improved commercial process for preparing naproxen from a naphthalene derivative comprising
    (a) reacting under Friedel-Crafts conditions 1-chloro-2-methoxy-naphthalene with propionyl chloride in methylene chloride at a temperature of from about 0° C. to ambient temperature in the presence of aluminum chloride to form 1-(5-chloro-6-methoxy-2-naphthyl)-1-propanone,
    (b) using directly, without isolation or purification, the reaction products of step (a), including 1-(5-chloro-6-methoxy-2-naphthyl)-1-propanone, to react with natural tartaric acid or its derivatives to form a compound of the formula

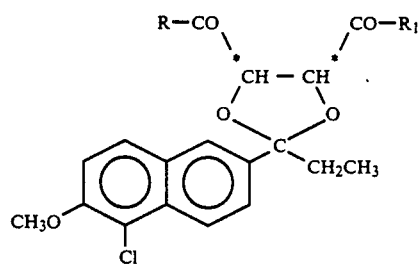

wherein R and R$_1$, which can be identified or different, represent hydroxy, alkoxy, amino, substituted amino, or O-M$^+$ wherein M$^+$ is the cation of an alkaline or an alkaline earth metal or ammonium;
    (c) brominating the reaction product of step (b) to form a compound of the formula

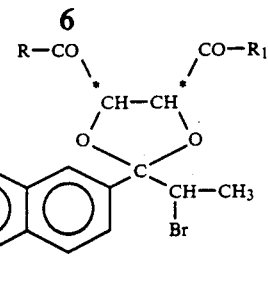
wherein R and $R_1$ are as previously defined;
(d) subjecting the compound of step (c) to rearrangement in water at acid pH to obtain (2S)-2-(5-chloro-6-methoxy-2-naphthyl)-propionic acid; and
(e) subjecting the compound of step (d) to hydrogenolysis to remove the 5-chloro group and form naproxen.
* * * * *